United States Patent
Simmons et al.

(10) Patent No.: US 6,817,993 B1
(45) Date of Patent: Nov. 16, 2004

(54) ABSORBENT ARTICLE INCORPORATING LIQUID BARRIERS WITH SEALING COATING

(75) Inventors: Eva Simmons, Mölndal (SE); Peter Rönnberg, Mölndal (SE); Anders Gustafsson, Billdal (SE); Bo Runeman, Jonsered (SE)

(73) Assignee: SCA Hygiene Products AB, Goteborg (SE)

( * ) Notice: Subject to any disclaimer, the term of this patent is extended or adjusted under 35 U.S.C. 154(b) by 0 days.

(21) Appl. No.: 09/380,211

(22) PCT Filed: Feb. 25, 1998

(86) PCT No.: PCT/SE98/00339

§ 371 (c)(1),
(2), (4) Date: Nov. 8, 1999

(87) PCT Pub. No.: WO98/37841

PCT Pub. Date: Sep. 3, 1998

(30) Foreign Application Priority Data

Feb. 26, 1997 (SE) ............................................... 9700696

(51) Int. Cl.[7] .............................................. A61F 13/20
(52) U.S. Cl. ............................. 604/385.27; 604/385.04; 604/385.28
(58) Field of Search .............................. 604/358, 381, 604/385.01, 382, 385.101, 385.08, 367, 385.09, 385.14, 385.24, 385.31, 386–387, 385.27, 385.28

(56) References Cited

U.S. PATENT DOCUMENTS

| | | | |
|---|---|---|---|
| 3,906,951 A | | 9/1975 | Ling |
| 4,795,454 A | * | 1/1989 | Dragoo .................... 604/385.2 |
| 5,304,160 A | * | 4/1994 | Igaue et al. ............ 604/385.28 |
| 5,342,342 A | * | 8/1994 | Kitaoka .................. 604/385.19 |
| 5,344,516 A | * | 9/1994 | Tanji et al. ................. 156/164 |
| 5,439,459 A | | 8/1995 | Tanji et al. |
| 5,445,627 A | | 8/1995 | Mizutani et al. .......... 604/385.2 |
| 5,607,760 A | * | 3/1997 | Roe ............................ 442/375 |
| 5,669,902 A | * | 9/1997 | Sivilich ...................... 604/396 |
| 6,152,908 A | * | 11/2000 | Widlund et al. ........ 604/385.19 |
| 6,156,024 A | * | 12/2000 | Schulte et al. .......... 604/385.28 |

FOREIGN PATENT DOCUMENTS

| | | |
|---|---|---|
| EP | 0374640 A2 | 6/1990 |
| EP | 0 745 367 | 12/1996 |
| JP | 02-031756 | 2/1990 |
| WO | 95/16424 | 6/1995 |
| WO | 96/16681 A1 | 6/1996 |
| WO | 97/05908 A2 | 2/1997 |
| WO | 98/24391 A2 | 6/1998 |
| WO | 98/37841 A1 | 9/1998 |

* cited by examiner

*Primary Examiner*—John J. Calvert
*Assistant Examiner*—Michele Kidwell
(74) *Attorney, Agent, or Firm*—Burns, Doane, Swecker & Mathis, L.L.P.

(57) ABSTRACT

An oblong absorbent article that includes a liquid-impermeable bottom sheet, and upper liquid-permeable sheet and an absorbent body disposed between these sheets, and on each side of the longitudinal center line of the upper sheet at least one longitudinal elastic liquid barrier having at least the free edge treated with a non-adhesive sealing medium which partly fills out the pores formed between the free edge and the abutment surface on the wearer, and/or which, when the article is donned, increases around said abutment surface, the wetting angle of the liquid to the skin. An absorbent article that includes an essentially liquid-impermeable top sheet above an absorbent body enclosed between an upper liquid-permeable sheet and a liquid-impermeable sheet, the top sheet being provided with elastic for shaping the article to the wearer's body and incorporating apertures intended to register with the anus and the urethra orifice of the wearer in use, around which apertures elastically puckered sealing edges are disposed, at least one sealing edge being coated with the sealing medium.

4 Claims, 19 Drawing Sheets

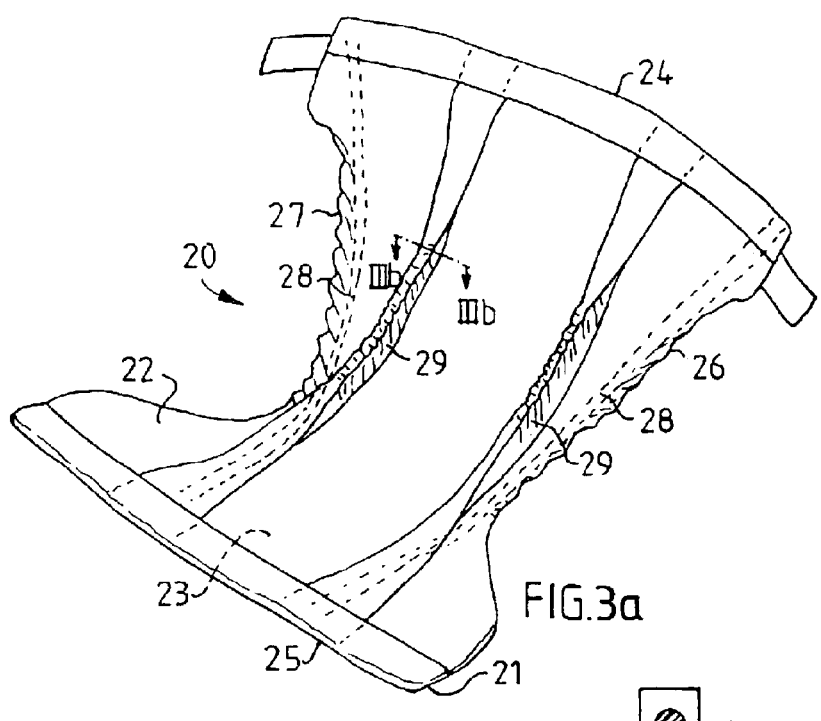
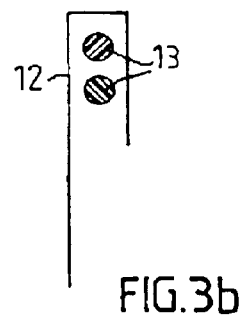

$$\varnothing D = \frac{10}{240} = 0.04176 \text{ mm}$$

$L_{fil} = 32$ mm $L_{fob} = 50$ mm $\emptyset D = \frac{39}{240} = 0.1625$ mm $L_{fil} = 83$ mm $L_{fob} = 130$ mm $$\emptyset D = \frac{58}{240} = 0{,}24167 \text{ mm}$$

$$L_{fil} = 95 \text{ mm}$$

$$L_{fob} = 205 \text{ mm}$$

$\emptyset D = \frac{70}{240} = 0.29167$ mm $L_{fil} = 155$ mm $L_{fob} = 245$ mm $\varnothing D = \frac{70}{240} = 0{,}29167$ mm $L_{fil} = L_{fob}$

ABSORBENT ARTICLE INCORPORATING LIQUID BARRIERS WITH SEALING COATING

The present invention relates to absorbent articles, such as diapers or incontinence guards, which seal more effectively against the wearer than earlier known articles of this kind.

An absorbent article of the kind to which the invention relates comprises a liquid-impermeable sheet which is intended to lie distal from the wearer in use, an absorbent body, and an upper liquid-permeable sheet which is intended to lie proximal to the wearer in use. When the absorbent article is a diaper or an incontinence guard it will also include flexible side flaps or wings that extend laterally outside the absorbent body on both sides thereof, and elastic elements that extend longitudinally along the free side-edges of the side-flaps at least within that part which is intended to form the crotch part of the article in use, said side flaps and elastic elements functioning to enable the absorbent article to be fitted to the wearer. These elastic elements function as leg elastic when the article is worn. Thus, when the article is donned, the elastic elements will be stretched and hold the side flaps tightly against the wearer.

Currently available absorbent articles have very high absorbencies and can also retain liquid under pressure. The most serious problem occur in the event of rapid liquid discharges. In such cases, it is necessary for a large volume of liquid to pass first through the top liquid-permeable sheet and then be absorbed by and dispersed in the absorbent body. This does not take place instantaneously. The time taken for the liquid to pass through the top sheet may be from about 1 to 2 minutes, during which time liquid will run out to the edges of the article and leak therefrom. These problems are addressed with the aid of so-called liquid barriers or inner cuffs or side-flaps that are intended to resist liquid leakage in the event of rapid liquid discharges. The originally used cuffs where intended primarily to retain faeces and were formed by folding a part of the liquid-permeable top sheet around an elastic thread. In recent times, manufacturers have begun to produce the cuffs from a liquid-impervious material in order to also retain liquid.

When the leg elastic on the absorbent article is stretched and the article fastened on the wearer, the elastic element of the liquid barriers will also be stretched, thereby raising the barriers up. The elastic element of the barriers will hold the barrier edges under tension against the wearer. The upstanding liquid barriers then form beneath the wearer a "trough" in which a rapidly discharged large volume of urine can be accommodated during the time required for the liquid to pass through the top liquid-permeable sheet. Attempts to improve the effectiveness of such liquid barriers have hitherto been directed towards the use of denser materials and towards flaps of sufficiently large size.

One drawback, however, is that liquid will rise above the brim of the barriers and leak out when the volume of liquid discharged is excessive or when the wearer sits or lies down such as to press together the space between the upstanding liquid barriers.

Thus, currently available absorbent articles, such as diapers or incontinence guards, may include along the outer longitudinal edges of the article sealing edges that are intended to lie tightly around the wearer's thighs and to shape the article to the wearer's body, as well as a pair of inner cuffs or liquid barriers which lie inwardly of the outer longitudinal edges and which are intended to form an impervious barrier against rapidly discharged liquid that is not absorbed immediately by the absorbent body of said article. These inner cuffs shall thus be capable of withstanding a relatively high liquid pressure over a limited time period in the order of a minute or so. The liquid will have been absorbed by the absorbent body when this time period has passed. Side cuffs may also be used on sanitary napkins, for instance. Also available are articles which include transverse cuffs that seal-off the transverse edges of the absorbent body.

Absorbent articles which lack the aforedescribed inner liquid barriers are also available. In these cases, the outer longitudinal sealing edges form the sole liquid barriers of the absorbent body.

Also available are absorbent articles which include a liquid-impermeable sheet that is intended to lie proximal to the wearer in use and that incorporate elastic threads for shaping the article to the wearer's body. This liquid-impermeable sheet includes at least one aperture which is intended to register with the wearer's anus and urethra orifice when the article is donned. Elastic is provided around at least a part of the perimeter of the aperture or apertures so as to shape the edges of the aperture against the wearer and to form a seal. Situated beneath the liquid-impermeable sheet is an absorbent body which is enclosed between a liquid-permeable sheet and a liquid-impermeable sheet, such that the absorbent body will hang down beneath the wearer with the liquid-impermeable sheet lying distal from the wearer.

The inner cuffs are comprised partly of a thin barrier sheet of essentially liquid-impervious and inelastic material, e.g. nonwoven material, and an elastic device which puckers or gathers together that edge of the liquid barrier which lies against the wearer. The unresilient, inelastic material is fastened along one longitudinal edge either to the top liquid-permeable sheet, so that no liquid can pass between these two sheets, or to the bottom liquid-impervious sheet along the side-edge of the article. The elastic device is fastened along the other edge of the unresilient material so as to gather the liquid barrier together and therewith form a puckered edge, which will extend or stretch partially when the article is donned. The puckered edge is normally comprised of an elastic thread which is placed in a channel in the inelastic material, said channel being formed by folding over and welding one edge of the material. When the absorbent article is donned, the puckered edge will stretch partially, the extent of this stretch being dependent on the size of the wearer and how the article is donned. It is also possible to use an elastic element consisting of an elastic film. In this case the elastic element will not be enclosed in a channel, but will be fastened, in a prestretched state, along a first longitudinal side-edge against the other side-edge of the unresilient material, the second side-edge of the element being free and abutting the wearer when the article is donned. Further, the first longitudinal side-edge of the elastic film may be fastened, in a prestretched state, directly against the top liquid-permeable sheet or the bottom liquid-impermeable sheet. In this case, the barriers will consist of solely the elastic film.

BRIEF DESCRIPTION OF THE DRAWINGS

Another type of sealing edges are described in U.S. Pat. No. 5,445,627. A sanitary napkin is provided with a pair of elastically stretchable flaps adjacent transversely opposite side edges. The flaps are in the form of straps and rising from a backsheet. Adhesives are applied on the top surface of said flaps so that the flaps may be adhesively fastened to the user's skin. The intention is to compensate for a shift of the basic body of the napkin relative to the wearer's body. Thus, the napkin is made to adhesively adhere to the user's skin. This is not a case where an elastic barrier element is stretched against the wearer-to obtain a good sealing effect.

In WO-A-9516424 a similar type of adhesive attachment of a sanitary napkin to the user is described. The object of the invention described is to provide an absorbent article that is adhesively secured to the wearer's body so that it will closely conform to and fit the external body surfaces. This is obtained by an absorbent article including an absorbent and a body side adhesive secured thereto and exhibiting suitable adhesion properties to skin but which can be removed without appreciable discomfort.

Neither U.S. Pat. No. 5,445,627 nor WO-A-9516424 describes elastic cuffs or liquid barriers which are stretched when the article is fastened on the wearer and where the elastic element will hold the barrier edges under tension against the wearer.

Figure 1B:
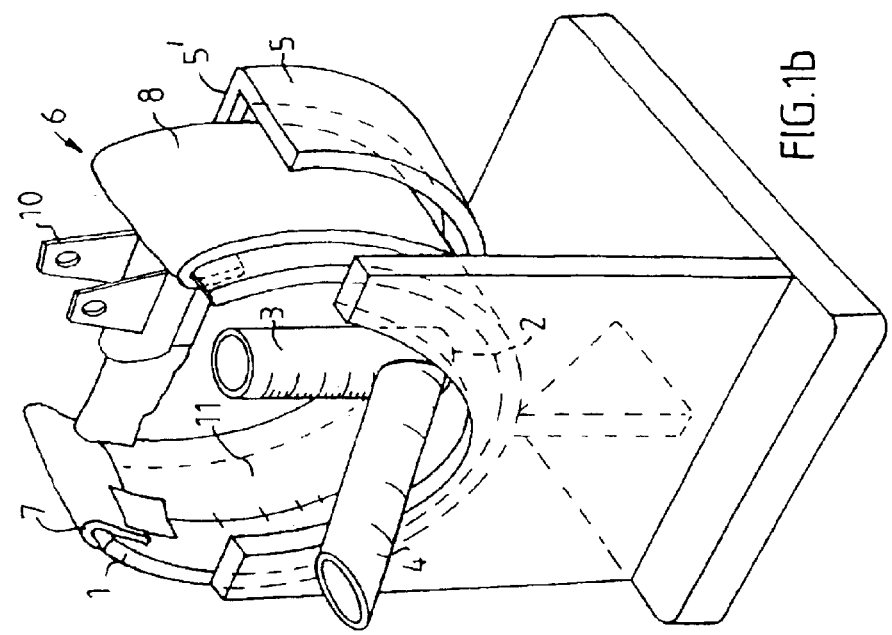
Figure 1A:
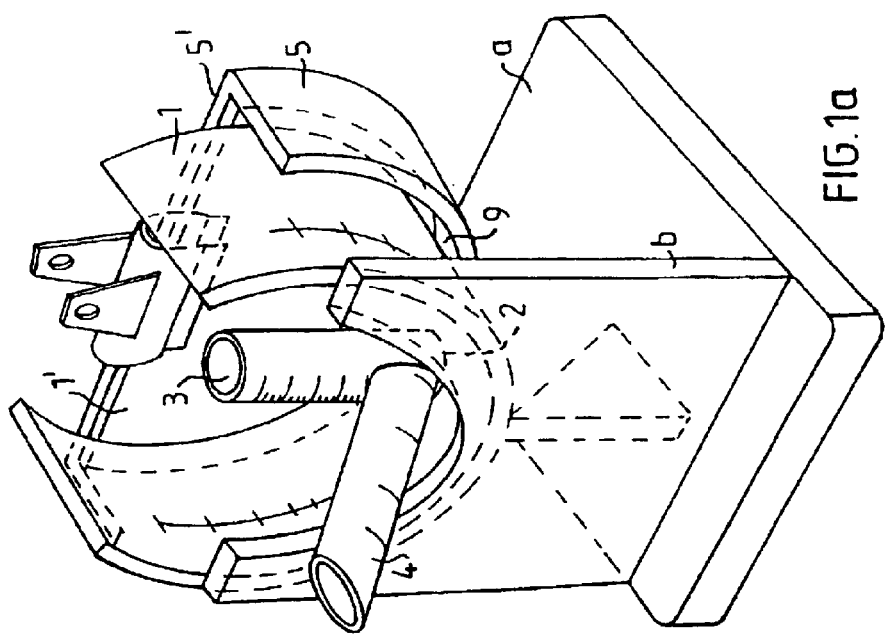
Figure 2A:
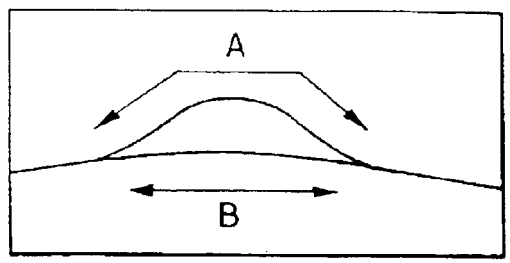
Figure 4A:
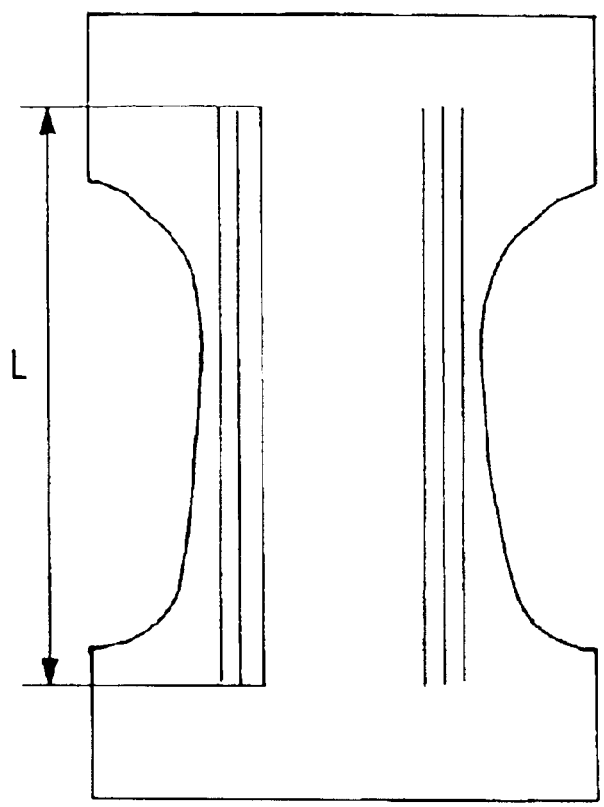
Figure 4B:
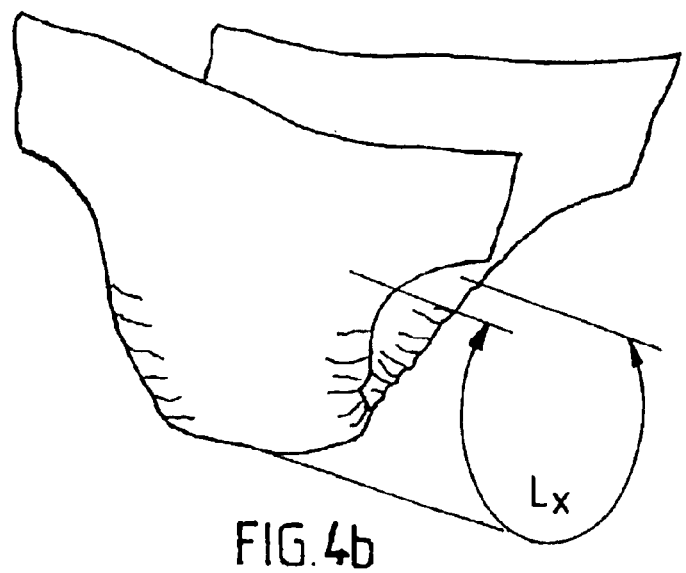
Figure 5A:
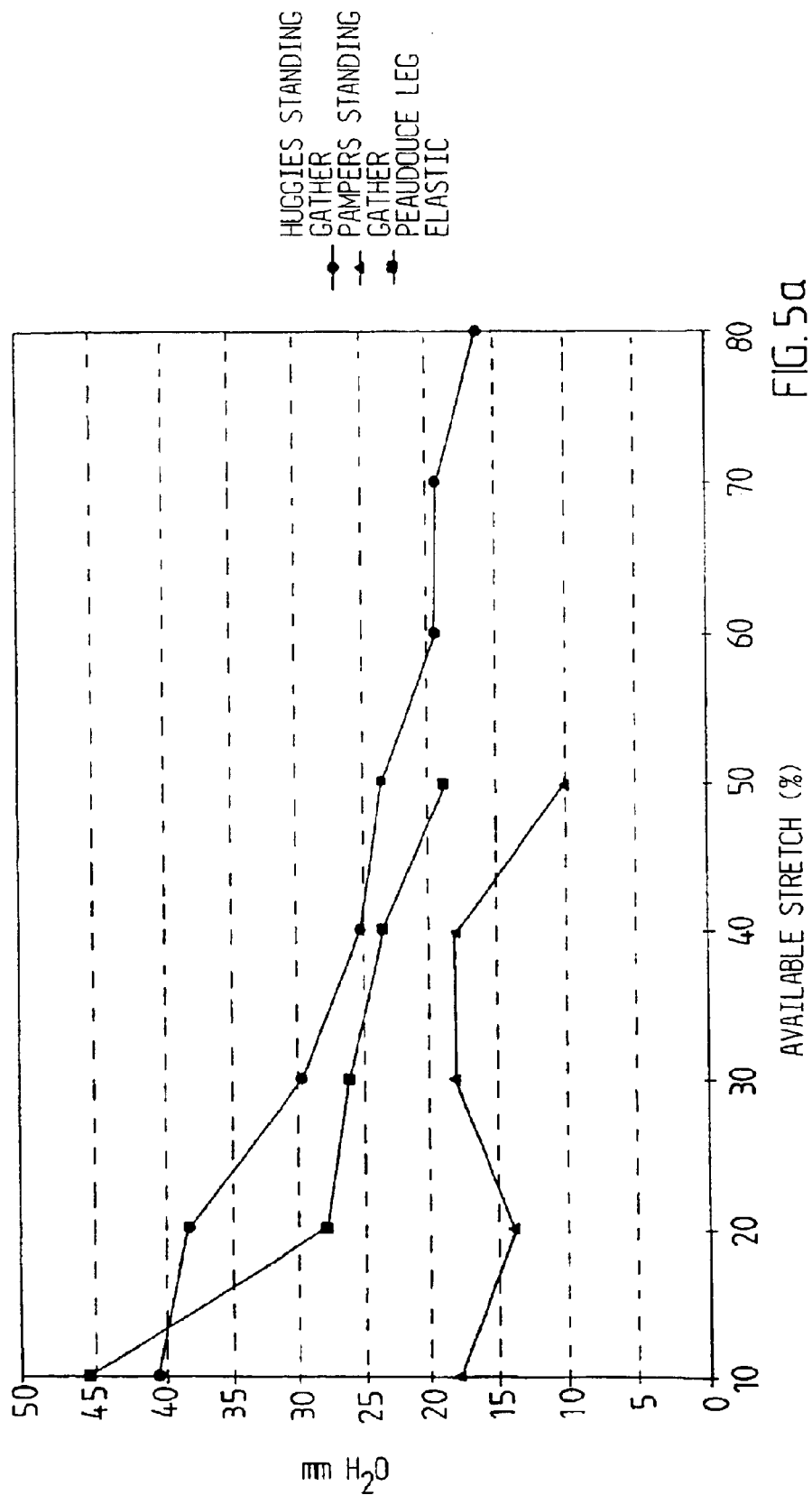
Figure 5B:
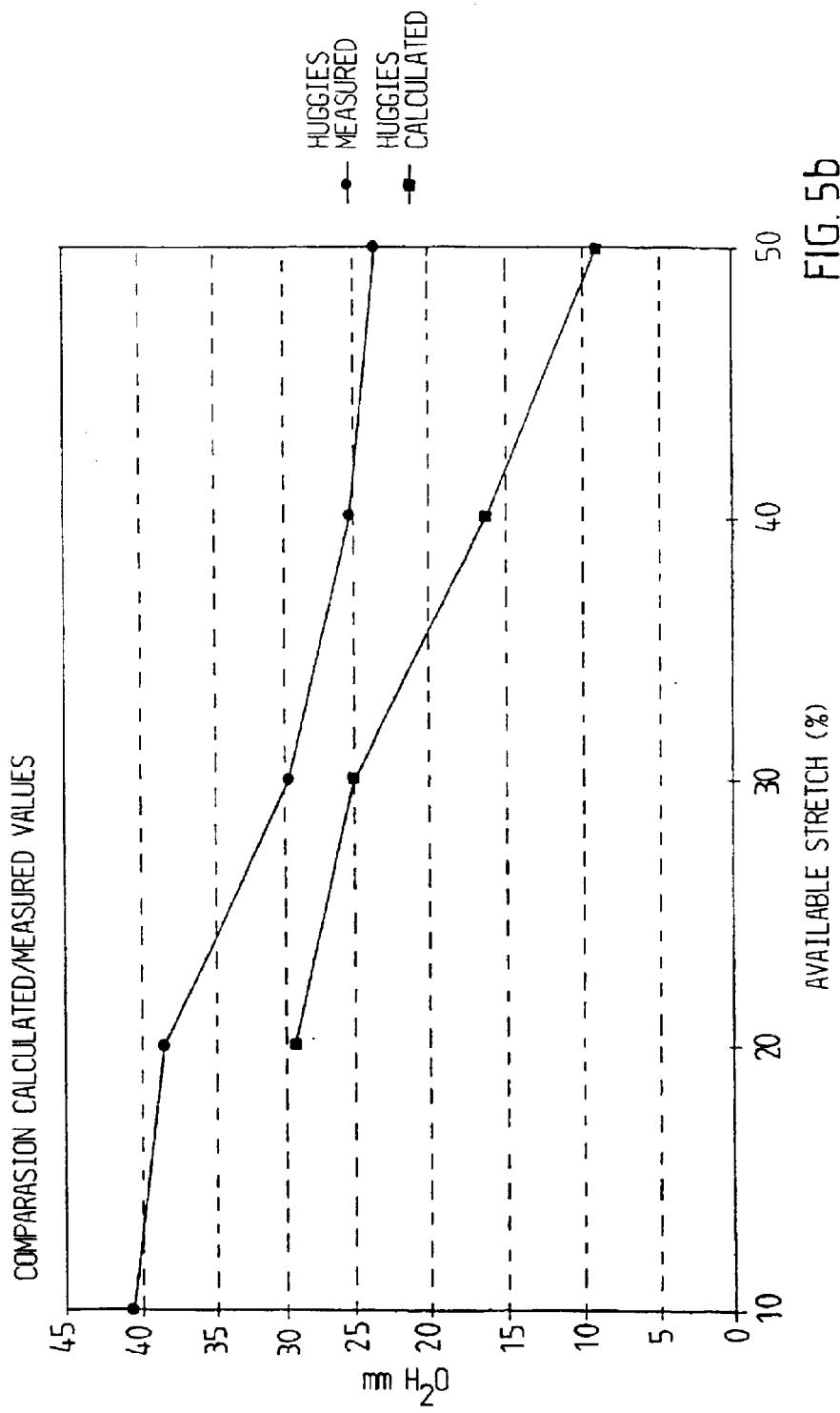
Figure 6:
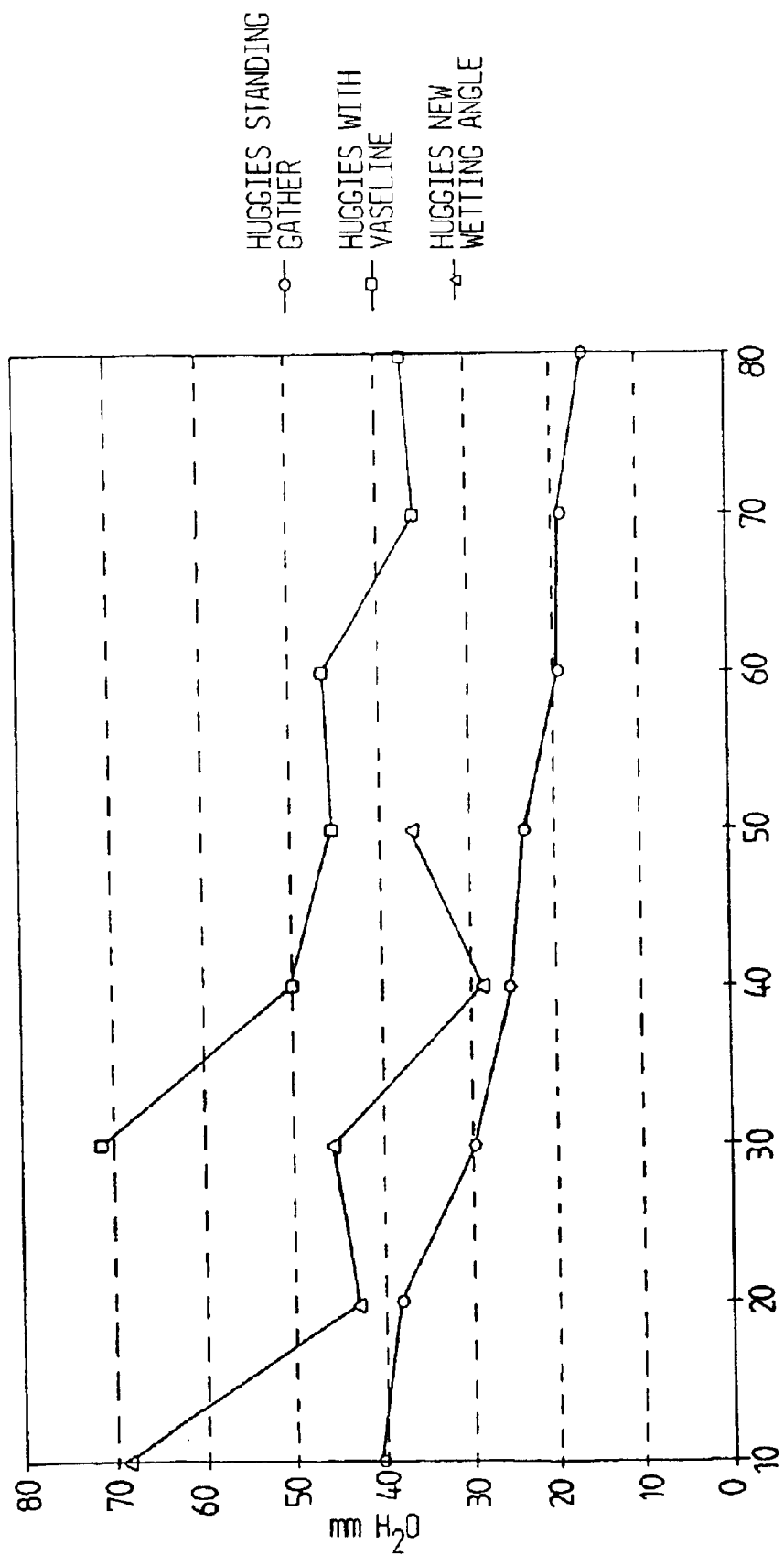
Figure 7:
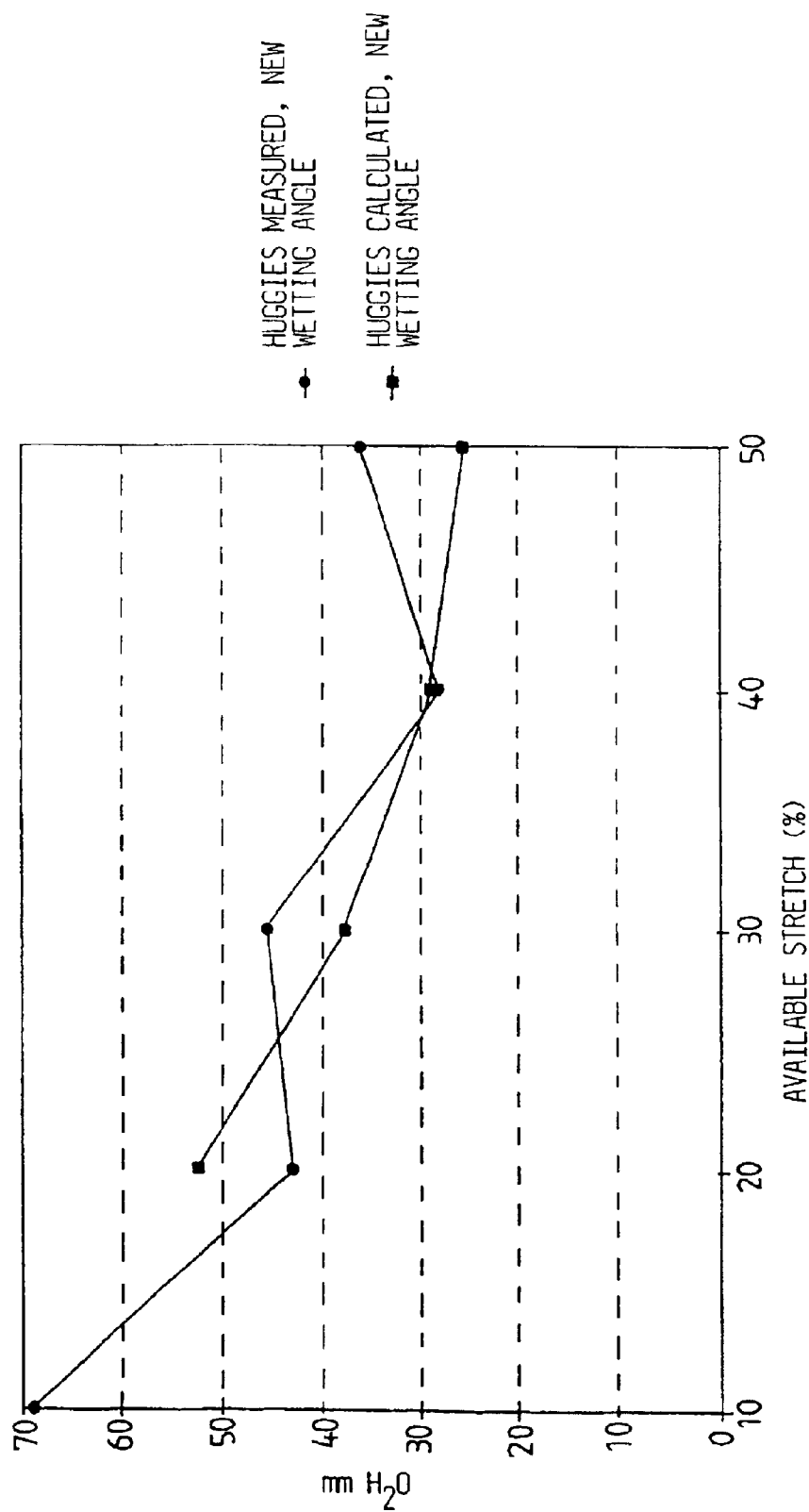
Figure 8:
Figure 8A:
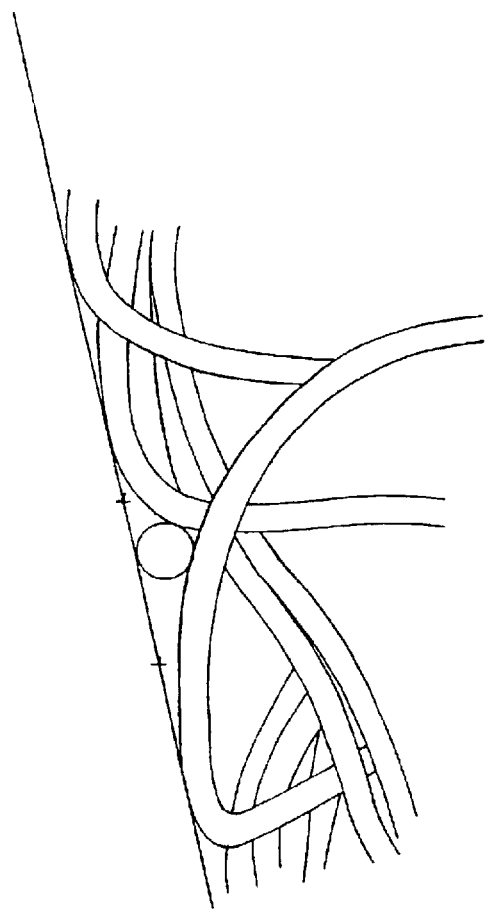
Figure 9:
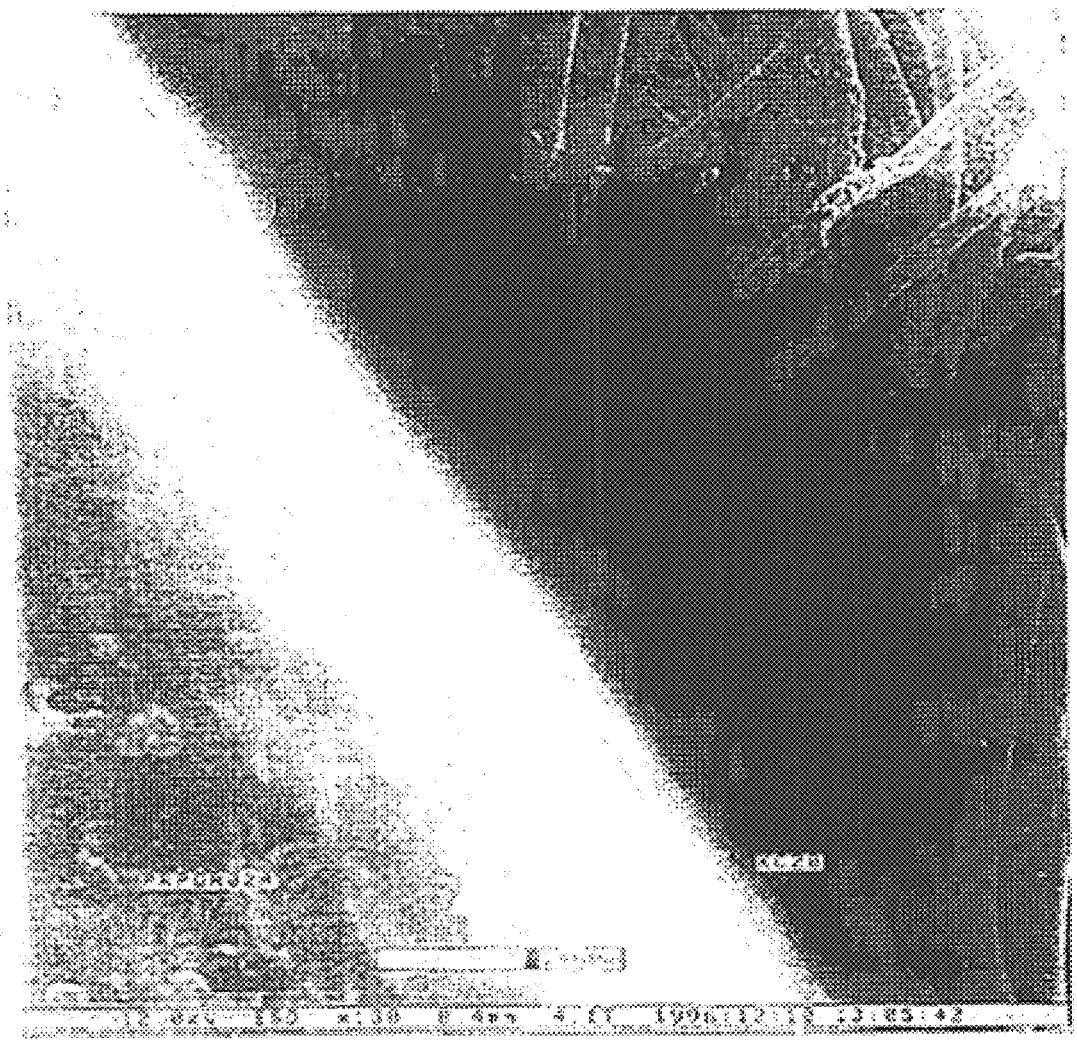
Figure 9A:
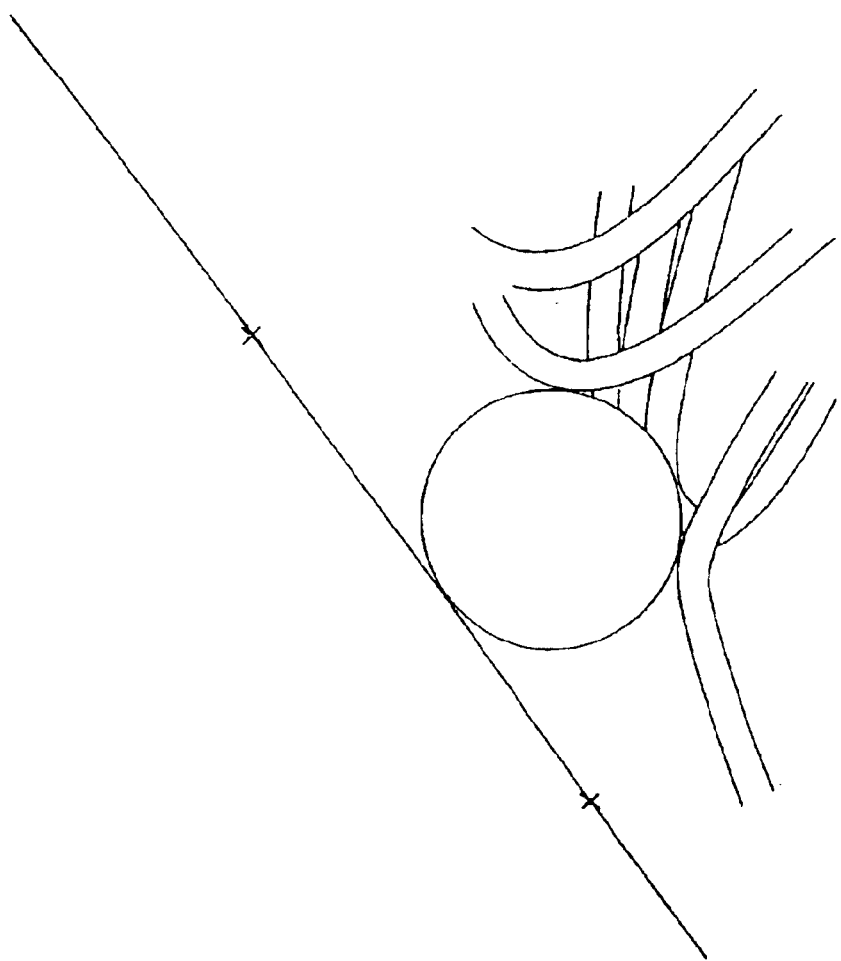
Figure 10:
Figure 10A:
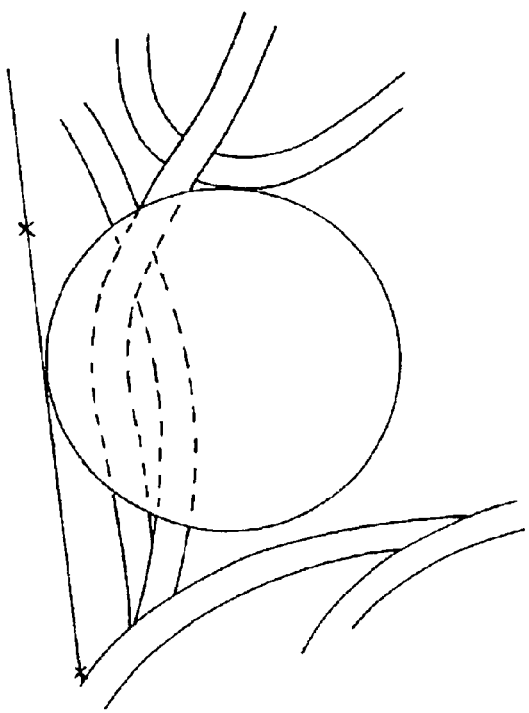
Figure 11:
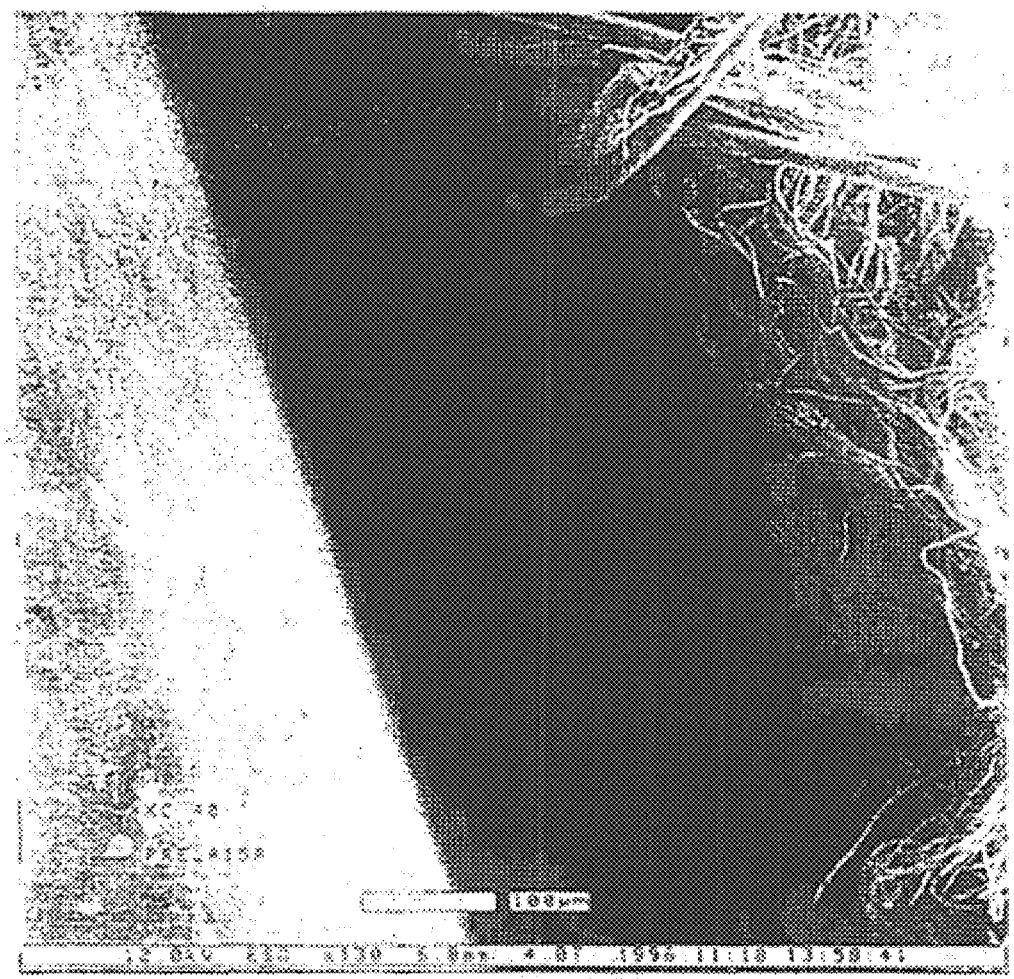
Figure 11A:
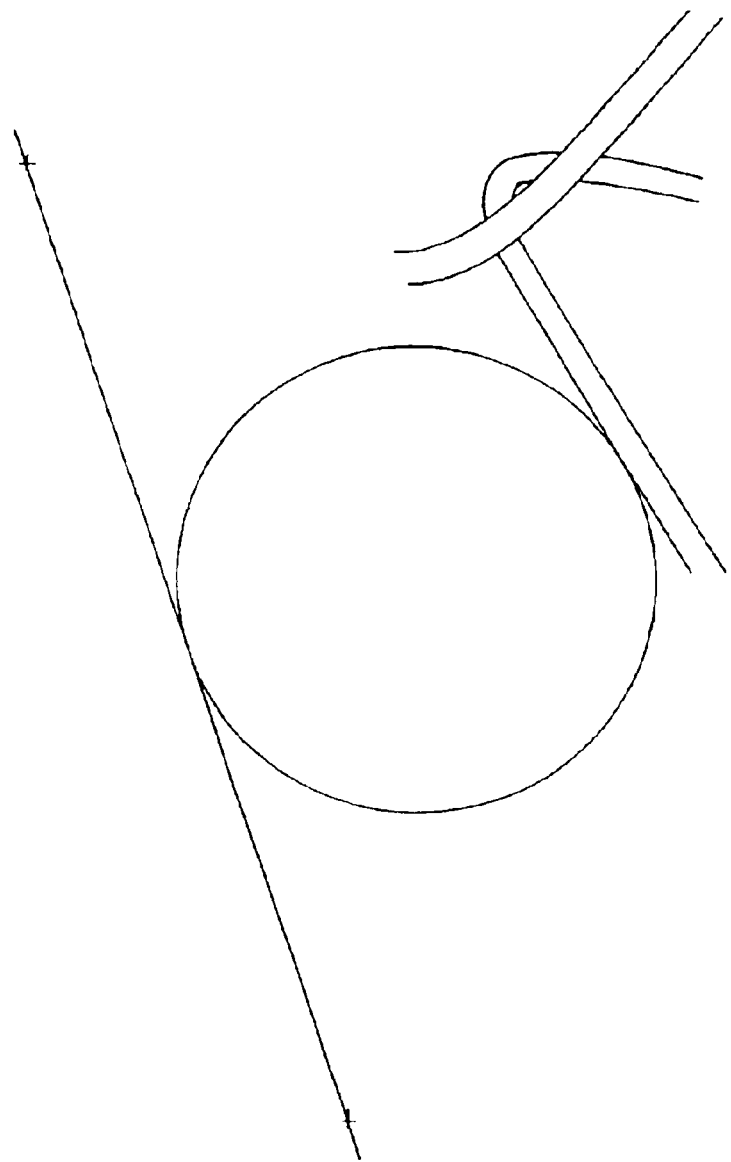
Figure 12:
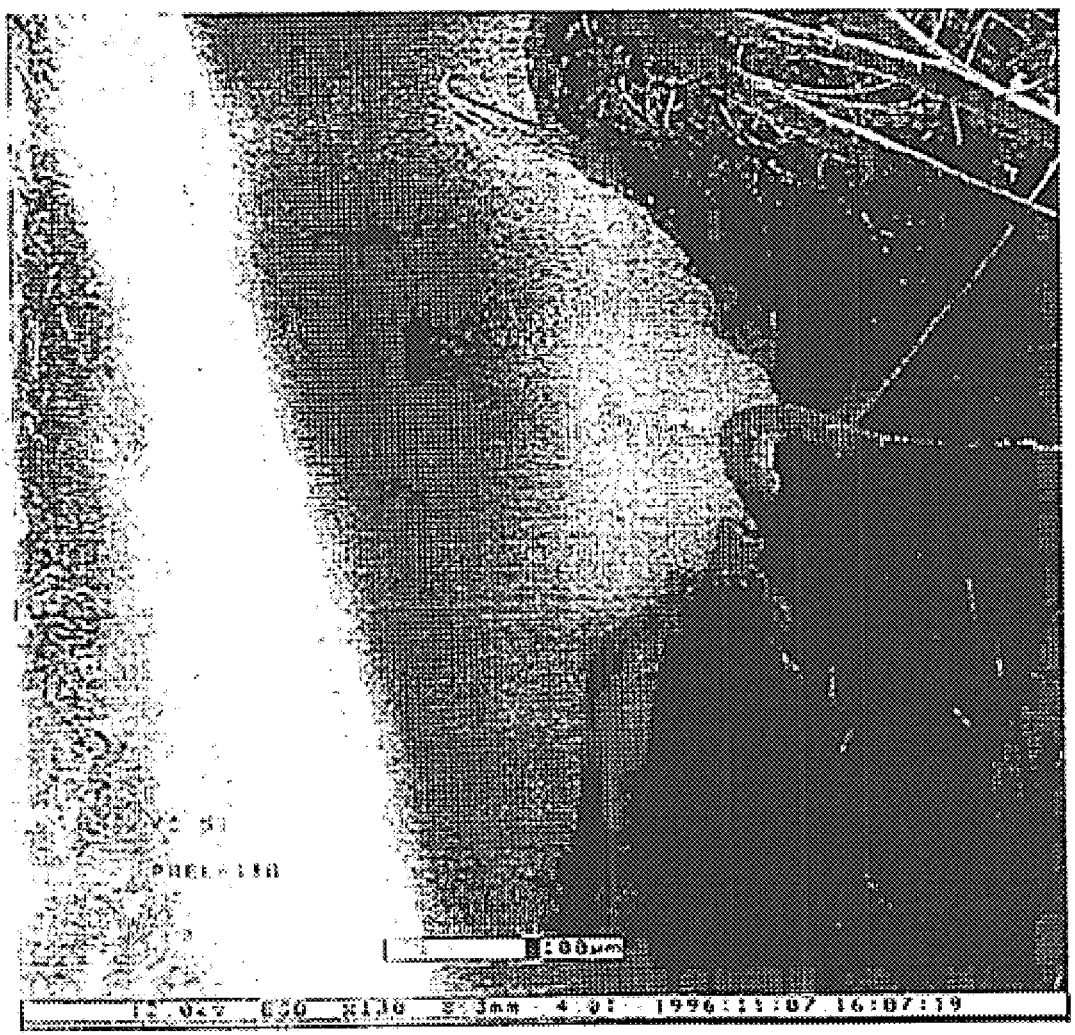
Figure 12A:
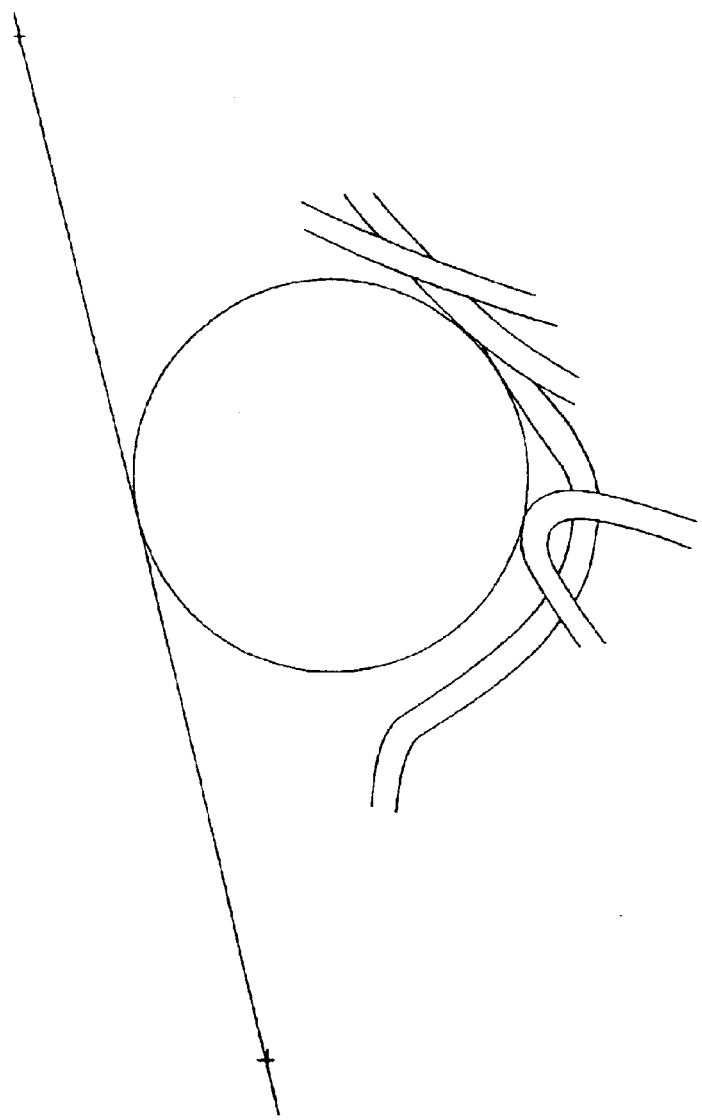

The invention will now be described with reference to the accompanying drawings, in which FIGS. 1a, b illustrate the measuring equipment used to determine the leakage pressure or breakthrough pressure without any material applied and with material applied in a stretched state, respectively, and 1c is a principle illustration of how the leakage pressure is determined;

FIGS. 2a, b illustrate schematically a pore in a liquid barrier and the principle of determining the weighted mean value cos θm and determining the radius r;

FIGS. 3a, b illustrate a conventional diaper or incontinence guard with upstanding liquid barriers;

FIGS. 4a, b illustrate the principle in which the available elongation or stretch is calculated;

FIG. 5a is a graphic illustration shoving the measured breakthrough pressures for three different liquid barriers;

FIG. 5b is a comparison diagram illustrating calculated and measured breakthrough pressures, respectively, for the best liquid barrier in FIG. 5a at different available degrees of elongation or stretch;

FIG. 6 illustrates the measured breakthrough pressure of a conventional upstanding liquid barrier and of two inventive embodiments;

FIG. 7 is a comparison diagram illustrating calculated and measured breakthrough pressures at different available elongations for one of the embodiments of the invention shown in FIG. 6;

FIGS. 8–13 are reproductions of photographs of different liquid barriers at different available elongations, taken with the aid of an electron microscope; and FIGS. 8a–12a are views corresponding to the photograph reproductions in FIGS. 8–12.

DETAILED DESCRIPTION OF THE INVENTION

An absorbent article, such as a diaper, is manufactured so that it can be used by persons of different sizes. This is achieved by gathering together, or puckering, liquid barriers and side-edges with the aid of elastic. These liquid barriers and side-edges will stretch to different extents in accordance with the size of the wearer, and the tension around the barrier edge will thus vary in dependence on the size of the wearer.

Tension in the barrier elastic can be expected to have significance in studies on the sealing property of a liquid barrier, and consequently the extent to which the barrier is stretched will also be significant.

The term available elongation or stretch can be used when considering the extent to which a liquid barrier is stretched.

In the manufacture of the absorbent article, e.g. a diaper, the elastic material, which has a given degree of stretchability, is fastened and "locked" firmly to the other non-stretchable materials, normally nonwoven. The extent to which the elastic material is stretched in the manufacture of the article cannot be exceeded when the article is in use, since the elastic material is firmly locked to a non-stretchable material. This is shown in FIG. 4a. The elastic material has the length L at this point.

A diaper is puckered somewhat when placed on the wearer's body. The elastic material has then been contracted to the smaller length Lx.

The available stretch or elongation X is the extent to which the material can be stretched from the user state to the maximum stretched state of the product. This can be expressed by the formula: $L=Lx((X/100)+1)$, where X is the available stretch or elongation in percent.

Figure 1C:
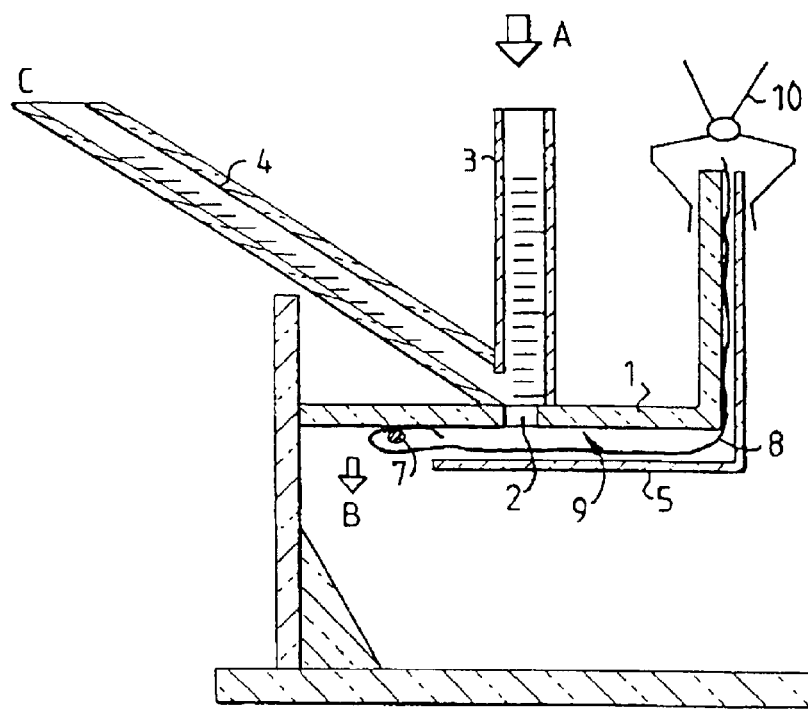

Test equipment was constructed with the intention of studying the sealing effect achieved between a liquid barrier or some other puckered barrier and the wearer's skin. This equipment is shown in FIGS. 1a, 1b and 1c and comprises a Plexiglas stand which includes a base plate a and an upstanding support plate b. A first upwardly open, semi-cylindrical element 1 is fastened horizontally to the upstanding support plate b and has around its periphery 11 a scale which denotes the available elongation or stretch. One end of the semi-cylindrical element is attached to the support plate while the other end has an end-wall 1'. Provided at the very bottom of the semi-cylindrical element 1 is a hole 2 to which a vertically upstanding filling tube 3 and an inclined measuring tube 4 lead, both of said tubes having a scale expressed in mm water. The equipment also includes a loose second semi-cylindrical element 5 whose diameter is somewhat larger than the diameter of the first semi-cylindrical element 1 and which has one side open and an end-wall 5' at its other end.

As shown in FIG. 1b, a measuring operation is carried out by securing a liquid barrier 6 around the outer periphery of the first semi-cylindrical element and fastening said barrier around the upper edges. The elastic part 7 is directed towards the attachment of the semi-cylindrical element to the support plate b, and the liquid barrier material 8 is folded around the end-wall 1' of the first semi-cylindrical element 1 on the other side. The elastic part is fastened along the scale on the semi-cylindrical element so as to enable the available elongation or stretch to be read-off. The end-wall 5' of the second semi-cylindrical element 5 is placed against the end-wall 1' of the first semi-cylindrical element with said upfolded part of said barrier material 8 located therebetween and pressed thereagainst with the aid of a clamp 10, such as to obtain a small clearance 9 between the cylindrical walls. Synthetic urine is introduced through the vertical tube 3. The liquid barrier is first weighted down so as to fill the clearance between the semi-cylindrical elements. A liquid pressure is thereafter built-up against the elastic edge 7 at the same time as a liquid column is formed in the tubes 3, 4, where the pressure can be read-off. Liquid is introduced until leakage occurs at arrow B (FIG. 1c) at the breakthrough pressure.

Two available types of liquid barriers, Huggies standing gather and Pampers standing gather, and a liquid barrier still not in production, Peaudouce leg elastic, were studied with this equipment, the leakage tendency being measured with the elastic element stretched to and locked at different available elongations. The liquid pressure at which leakage will occur in respect of a barrier stretched to a given extent, i.e. a barrier that has a given available elongation or stretch, has been determined with the aid of the test equipment and was found to vary in dependence on the extent to which the puckered or gathered edge is stretched. The measured values are shown in the diagram in FIG. 5a. As will be evident from the Figure, however, different barriers give different breakthrough pressures at the same available stretch or elongation. It thus appears that the sealing effect is influenced by factors other than solely the tension in the elastic material.

The invention takes as its starting point an attempt to provide an improved sealing effect on the basis of factors other than the actual tension in the elastic.

On the basis of the theory that leakage does not occur merely because the elastic in the barrier material releases its contact with the wearer's skin, but occurs primarily through the through-penetrating pores or channels that are formed between the wearer's skin and the folds in the puckered or gathered edge of the barrier material, endeavors have been made to create a model from which the leakage pressure can be determined theoretically and thereby become aware of those parameters that shall be influenced in order to achieve an improved sealing effect.

The capillary pressure of the pores in porous structures can be calculated with the Laplace equation.

According to Laplace, the capillary pressure $\Delta P = 2\gamma \cos \theta / r$, where $\gamma$ is the surface tension of the liquid, $\theta$ is the wetting angle of the liquid to the material in the capillary walls, and r is the radius of the capillary. When $\theta$ is greater than 90°, $\cos \theta$ is negative and $\Delta P$ is consequently also negative. The capillary wall is hydrophobic and the resultant pressure $\Delta P$ can be said to describe the breakthrough pressure, i.e. the maximum pressure a capillary or pore can withstand, When $\theta$ is less than 90°, the capillary wall is hydrophilic and $\Delta P$ and $\cos \theta$ are positive. Liquid is then "sucked" into the pores.

When studying the pressure in a capillary or pore where the wall consists of several materials, such as in a pore formed between skin and a fold in a liquid barrier, the proportion of circumference of each material must be weighed together so as to provide a mean value of $\cos \theta$, hereinafter designated $\cos \theta m$. The breakthrough pressure will then be $\Delta P = 2\gamma \cos \theta m / r$.

In the present case, the walls of the pores consist partly of an hydrophilic material, i.e. skin, which has a wetting angle of less than 90°, and partly of the hydrophobic material in the liquid barrier, which has a wetting angle above 90°. Cos $\theta m$ is the weighted mean value of the pore wall's cos $\theta$-values and is calculated in the manner illustrated in FIG. 2a, where A designates the circumference proportion hydrophobic wall and B designates the circumference proportion hydrophilic wall, where A+B=1. Cos $\theta m$ will there equal $A \cdot \cos \theta_{fob} + B \cdot \cos \theta_{fil}$.

As described below, trials have been carried out with the intention of checking whether or not the described model can be used as a basis on which the breakthrough pressure can be determined.

The wetting angle of the skin varies in accordance with the state of the skin, i.e. whether the skin is clean or dirty for instance. Measuring equipment comprised of Plexiglas with a wetting angle of 77°, which lies close to the mean value of the wetting angle of the skin (about 74°), was used for comparison purposes. Measurement were carried out on the commercial liquid barrier that produced the best sealing result according to FIG. 5a, i.e. Huggies standing gather which has a wetting angle of 120°.

The liquid used was synthetic urine. $\gamma$ is the surface tension of synthetic urine, i.e. 0.06 N/m.

Figure 2B:
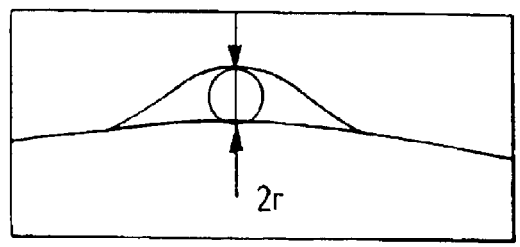

Abutment of a liquid barrier against the measuring equipment was studied at different available elongations with an electron microscope, enlargement 130 times, as illustrated in FIGS. 8–12 and FIGS. 8a–12a. As will be evident from the Figures, a through-penetrating pore is formed between the threads or fibres of the barrier material and the Plexiglas wall of the test equipment. This pore is assumed to function as a capillary, where r=the radius of the largest possible circle that can be enclosed in the channel, as evident from FIG. 2b.

The through-penetrating pore has been drawn in FIGS. 8a–12a The following pore radius values were obtained at different available elongations, as shown in the Figures.

| Available elongation | Pore radius |
| --- | --- |
| 10% | 0.0208 mm |
| 20% | 0.0812 mm |
| 30% | 0.1208 mm |
| 40% | 0.1458 mm |
| 50% | 0.1458 mm |

Comments: It was very difficult to measure the pore radius on the photograph at a 10% available elongation, and the value given is therefore perhaps unreliable.

The crosses shown in FIGS. 8a–12a show the lateral terminal points of the pore intended for calculating the hydrophobic and hydrophilic proportions of circumference of the pore. The length ratio between hydrophobic and hydrophilic surfaces in the pore at different available elongations is shown in the following Table.

| Avail. elong. | Hydr phil. surface | Hydrophob. surface |
| --- | --- | --- |
| 10% | 39% | 61% |
| 20% | 39% | 61% |
| 30% | 32% | 68% |
| 40% | 39% | 61% |
| 50% | 50% | 50% |

FIG. 5b shows a comparison between the breakthrough pressures mesured with the test equipment and the breakthrough pressures calculated with the aforesaid formula.

Since the calculated and measured breakthrough pressures are in good agreement, the sealing effect of an article against the wearer's skin can, thus, be improved by influencing $|\Delta P|$, i.e. $|2\gamma \cos \theta m / r|$ so that this value increases. One provision in this respect is that the tension in the elastic will be sufficiently high to prevent the liquid barrier from allowing liquid to escape at a lower pressure as a result of the elastic relaxing and allowing the barrier to "ease" away from the wearer by virtue of the liquid column weighing down the barrier so that it releases its contact with the abutment surface.

$|\Delta P|$ can be caused to increase by increasing the product $|(2\gamma \cos \theta m / r)|$ The object of the present invention is to provide an absorbent article with improved sealing against the wearer's skin.

This object is achieved with an absorbent article such as a diaper or an incontinence guard that includes a liquid-impermeable sheet which is intended to lie distal from the wearer in use, an upper liquid-permeable sheet which is intended to lie proximal to the wearer in use, an absorbent body disposed between said sheets, and on each side of the longitudinally extending center line of the liquid-permeable sheet at least one longitudinal elastic liquid barrier comprised of an essentially liquid-impervious material, where one longitudinal edge is free and faces towards the wearer and the other longitudinal edge is fastened to the upper liquid-permeable sheet along the longitudinal edge of the article or to the liquid-impermeable sheet at the longitudinal edge of said article, wherein at least the free edge of at least one liquid barrier on each side of the center line of the absorbent body is treated with a non-adhesive sealing medium which, in use, at least partly fills any through-penetrating pore formed between the free edge of the liquid barrier and the user abutment surface and/or which, when the article is donned, smears said abutment surface and thereby increases the wetting angle of the liquid to the skin.

The object of the invention is also achieved with an absorbent article that includes an essentially liquid impermeable sheet which is intended to lie proximal to the wearer in use and which incorporates elastic for shaping the article to the wearer's body, said sheet including an aperture which is intended to lie in register with the anus and urethra orifice of a wearer, wherein elastically gathered sealing edges are disposed around said apertures in the essentially liquid-impermeable sheet, wherein an absorbent body is disposed on that side of the essentially liquid-impermeable sheet that lies distal to the wearer in use, wherein the absorbent body is enclosed between a liquid-permeable sheet on the side proximal to the wearer and a liquid-impermeable sheet, wherein at least one sealing edge is treated with a non-adhesive sealing medium which, in use, at least partly fills out any through-penetrating pore formed between the free sealing edge and the abutment surface on a wearer, and/or which, when the article is donned, smears said abutment surface and thereby increases the wetting angle of the liquid to the skin.

When the non-adhesive sealing medium at least partly fills out a pore, the pore radius will decrease and the product $|(2\gamma \cos \theta m/r)|$ will increase. The same applies when an increased wetting angle is achieved.

The edge of the liquid barrier or the seating edge will conveniently be coated with sealing medium in an amount sufficient to both partly fill out the pores, i.e. decrease the pore radius, and to smear the skin of a wearer.

The sealing medium may be applied in a very thin layer, intended to be transferred to the wearer's skin when donning the article. However, the sealing medium will suitably be applied in an amount sufficient to reduce the pore radius and to smear the wearer's skin. The sealing medium may be applied in an amount corresponding to 0.1–100 g/m$^2$, suitably 1–30 g/m$^2$, particularly 2–20 g/m$^2$ and preferably 3–10 g/m$^2$. For instance, the sealing medium may be applied in an amount corresponding to about 20 g/m$^2$.

Since the skin is hydrophilic and has a mean wetting angle of about 74°, it is suitable for the sealing medium to at least increase this wetting angle to about 90°, so that the skin will be hydrophobic. The sealing medium will preferably have a wetting angle above 95°, and then particularly of at least 100°.

The sealing medium will preferably have rheological properties such as to be essentially rigid or viscous at room temperature, and sufficiently fluid to smear the wearer's skin at body temperature. The sealing medium may not be so fluid as to run from the wearer's skin at body temperature and dirty the wearer's clothes. Neither should the sealing medium be excessively rigid at room temperature, since it would then be able to loosen from the liquid barrier or the sealing edge in lumps or "crumbs". The person skilled in this art will be able to determine after laboratory testing which sealing media that have appropriate theological properties.

In addition to the sealing medium needing to have the correct viscosity and flow properties required to fill-out cavities, have the correct surface energy for the liquid barrier function, it will also preferably be unable to penetrate the skin or to emit harmful substances or have any other negative effect on the normal function of the skin. Neither may the properties of the sealing medium change in the passage of time.

The sealing medium will also preferably contribute towards reducing friction against and/or wearing of the skin.

To this end there can be used ointments that include fat/oil of animal, vegetable or petrochemical origin. Examples of such ointments are Silonsalva (Perstorp Pharma), petrolatum (Vaseline ®).

It is also possible to use water/oil emulsions, which are hydrophobic.

Other possible sealing media are, for instance, preparations which are semisolid or solid at 20° C. and which comprise 10–95% of a polysiloxane plastiziser that has a plastic or flowing consistency at 20° C., and 5–90%, preferably 5–50% of an agent that can cause the plastiziser to solidify on the barrier, said agent suitably having a melting point of at least 35° C., preferably at least 40° C., and consisting of fatty acid esters or fatty acid amides having several hydroxyl groups, fatty alcohols having 14–22 carbon atoms, fatty acids having 12–22 carbon atoms, fatty alcohol ethoxylates having 12–22 carbon atoms, or a mixture thereof. Suitable sealing media are described in WO 96/16681.

The sealing medium used must be dermatologically acceptable and may not cause irritation or allergical reactions.

One advantage of the inventive article is that it will slide more readily against the wearer's skin and therewith cause less irritation than conventional articles of this kind.

The invention will now be described in more detail with reference to the particular embodiments thereof and also with reference to the accompanying drawings.

EXAMPLE

FIG. 3a shows a conventional diaper or incontinence guard 20 which includes a liquid-permeable top sheet 22, an absorbent sheet 23, and a liquid-impermeable bottom sheet 21, said sheets being delimited by two transverse edges 24, 25 and two longitudinal edges 26, 27. The illustrated article also includes longitudinally extending leg elastic 28 and an upstanding liquid barrier 29 on each side of the longitudinal center line. FIG. 3b is a sectional view that illustrates the construction of the upstanding liquid barrier comprising a liquid-impermeable sheet 12 whose free edge is curved around two stretched elastic threads 13. The threads 13 function to pucker the sheet 12.

The wetting angle was changed in two tests. In the first case, a plastic film having a wetting angle of 97.5° was stretched over the first semi-cylindrical Plexiglas surface. This corresponds to such a treatment of the barrier that the wearer's skin will obtain a higher wetting angle therefrom. This is hydrophobic in distinction to the normal skin mean wetting angle of about 74°. The result of this change in wetting angle (center curve) is compared in FIG. 6 with the sealing effect achieved with the upstanding liquid barrier Huggies standing gather (lowermost curve). As the measuring values show, an improved sealing effect is achieved in this way.

The uppermost curve in FIG. 6 shows measurements obtained with a liquid barrier that had been treated with Vaseline®. Vaseline® has a wetting angle of 100°. The Vaseline® partially blocks the pores, i.e. reduces the pore radius, and smears the wearer's skin, thereby increasing the wetting angle of the skin. As will be evident from the diagram shown in FIG. 6a, there is obtained a significant improvement that exceeds the improvement achieved when only the wetting angle of the skin is changed, despite obtaining, at the same time, a reduction in the wetting angle of the barrier by virtue of the Vaseline® also smearing the liquid barrier and therewith lowering its wetting angle from 120° to 100°.

FIG. 7 is a diagram in which the calculated and measured sealing values obtained when changing the wetting angle are shown. The measured values have been obtained by covering the Plexiglas with the aforedescribed plastic film, and corresponds to the centre curve in the diagram shown in FIG. 6. Good agreement is obtained between the calculated and measured values.

Figure 13:

FIG. 13 is a reproduction of an electron microscope photograph of a liquid barrier that has an available elongation or stretch of 30%, where the barrier material is coated with Vaseline®. This sealing medium has the sealing properties shown in the diagram of FIG. 6. It will be evident from the photograph that the fibers in the barrier material have a thick coating which increases the diameter of the fibers and thereby reduces the size of through-penetrating pores.

Although the invention has been described above with reference to certain concrete, non-limiting embodiments, it will be understood that the invention can be modified within the scope of the following claims. Particularly the outer barriers, i.e. the leg elastic, of articles that have no inner liquid barriers can be treated with a sealing medium. Both the inner and the outer barriers can also be treated in accordance with the present invention. In certain instances it may be beneficial to treat solely the outer barriers, even when the article includes inner liquid barriers. Transverse liquid barriers may also be treated with a sealing medium.

What is claimed is:

1. An absorbent article that includes longitudinally extending side extremities, an absorbent body disposed between a liquid-impermeable bottom sheet, which is intended to lie distal from a wearer in use, and a liquid-permeable upper sheet, which is intended to lie proximal to a wearer, and at least one longitudinally extending elastic liquid barrier on each side of a center line of the upper sheet, the barrier being made of an essentially liquid-impervious material and fastened to the upper or bottom sheet along or adjacent to a respective longitudinally extending side extremity of the article and having a free sealing edge facing towards a wearer, wherein only said sealing edge is treated with a non-adhesive sealing medium which, in use, at least partly fills out any through-penetrating pores which are formed between said sealing edge and an abutment part of a wearers skin, and/or which, when the article is donned, smears said abutment skin part and thereby increases a liquid-skin wetting angle.

2. The absorbent article according to claim 1, wherein said sealing edge is coated with said sealing medium in an amount sufficient to both partly fill out any through-penetrating pores and to smear said abutment skin part.

3. An absorbent article that includes longitudinally extending side extremities, an absorbent body disposed between a liquid-impermeable bottom sheet, which is intended to lie distal from a wearer in use, and a liquid-permeable upper sheet, which is intended to lie proximal to a wearer, and above the upper sheet, an essentially liquid-impermeable top sheet which is intended to lie against a wearer, and which includes elastic for shaping the article to a wearer's body, and includes apertures intended to lie in register with an anus and a urethra orifice of a wearer, around which apertures elastically puckered sealing edges are disposed in the top sheet;

wherein only said sealing edges are treated with a non-adhesive sealing medium which, in use, at least partly fills out any through-penetrating pores which may be formed between said sealing edges and an abutment part of a wearer's skin, and/or which, when the article is donned, smears said abutment skin part and thereby increases a liquid-skin wetting angle.

4. The absorbent article according to claim 3, wherein said sealing edges are coated with said sealing medium in an amount sufficient to both partly fill out any through-penetrating pores and to smear said abutment skin part.

* * * * *